(12) United States Patent
Gunther et al.

(10) Patent No.: US 9,500,576 B2
(45) Date of Patent: Nov. 22, 2016

(54) SYSTEMS AND METHODS FOR DETERMINING A VOLUMETRIC FLOW OF A LIQUID PORTION OF A MULTIPHASE FLUID FLOW

(71) Applicant: Yokogawa Corporation of America, Sugar Land, TX (US)

(72) Inventors: Frank Douglas Gunther, Fulshear, TX (US); Klaus Plattner, Sugar Land, TX (US)

(73) Assignee: Yokogawa Corporation of America, Sugar Land, TX (US)

( * ) Notice: Subject to any disclaimer, the term of this patent is extended or adjusted under 35 U.S.C. 154(b) by 411 days.

(21) Appl. No.: 14/048,594

(22) Filed: Oct. 8, 2013

(65) Prior Publication Data

US 2015/0100252 A1    Apr. 9, 2015

(51) Int. Cl.
  *G01N 9/36*  (2006.01)
  *G01N 9/32*  (2006.01)
  *G01F 1/74*  (2006.01)

(52) U.S. Cl.
  CPC ...... *G01N 9/36* (2013.01); *G01F 1/74* (2013.01); *G01N 9/32* (2013.01)

(58) Field of Classification Search
  USPC ........................................................ 702/50
  See application file for complete search history.

(56) References Cited

U.S. PATENT DOCUMENTS

| | | | | |
|---|---|---|---|---|
| 4,876,879 A | * | 10/1989 | Ruesch | G01F 1/74 73/32 A |
| 7,610,159 B2 | * | 10/2009 | Ito | G01F 25/0007 702/183 |
| 2008/0288181 A1 | | 11/2008 | Lucero | |
| 2012/0137754 A1 | * | 6/2012 | Henry | G01F 1/74 73/61.44 |

FOREIGN PATENT DOCUMENTS

| | | |
|---|---|---|
| GB | 2128756 A | 5/1984 |
| WO | 2003/021204 A1 | 3/2003 |
| WO | 2007/089412 A2 | 8/2007 |

OTHER PUBLICATIONS

International Search Report and Written Opinion for International Application No. PCT/US2014/023066 mailed Jul. 4, 2014.

* cited by examiner

*Primary Examiner* — Tung Lau
(74) *Attorney, Agent, or Firm* — Sutherland Asbill & Brennan LLP

(57) ABSTRACT

The disclosure generally relates to mass flow meters and more particularly relates to systems and methods for determining, among other things, a volumetric flow of a liquid portion of a multiphase fluid flow. In certain embodiments herein, an expected liquid density of a fluid flow at an operating condition may be determined. Such a determination may include receiving a measured density of the fluid flow and comparing the expected liquid density of the fluid flow to the measured density of the fluid flow. Further, a phase status of the fluid flow may be determined based at least in part on the expected liquid density compared to the measured density of the fluid flow.

4 Claims, 3 Drawing Sheets

1

SYSTEMS AND METHODS FOR DETERMINING A VOLUMETRIC FLOW OF A LIQUID PORTION OF A MULTIPHASE FLUID FLOW

TECHNICAL FIELD

The disclosure generally relates to mass flow meters, and more particularly, systems and methods for determining volumetric flow of a liquid portion of a multiphase fluid flow in mass flow meters.

BACKGROUND

A multiphase flow may be defined as a flow in which more than one phase (e.g., solid, gas, and/or liquid) occurs. In the oil and gas industry, typical multiphase fluid flows include gas-liquid flows and liquid-liquid flows. In many instances, it may only be desirable to know the volumetric flow of one of the phases of a multiphase flow.

BRIEF DESCRIPTION OF THE FIGURES

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION OF EXAMPLE EMBODIMENTS

Figure 1:
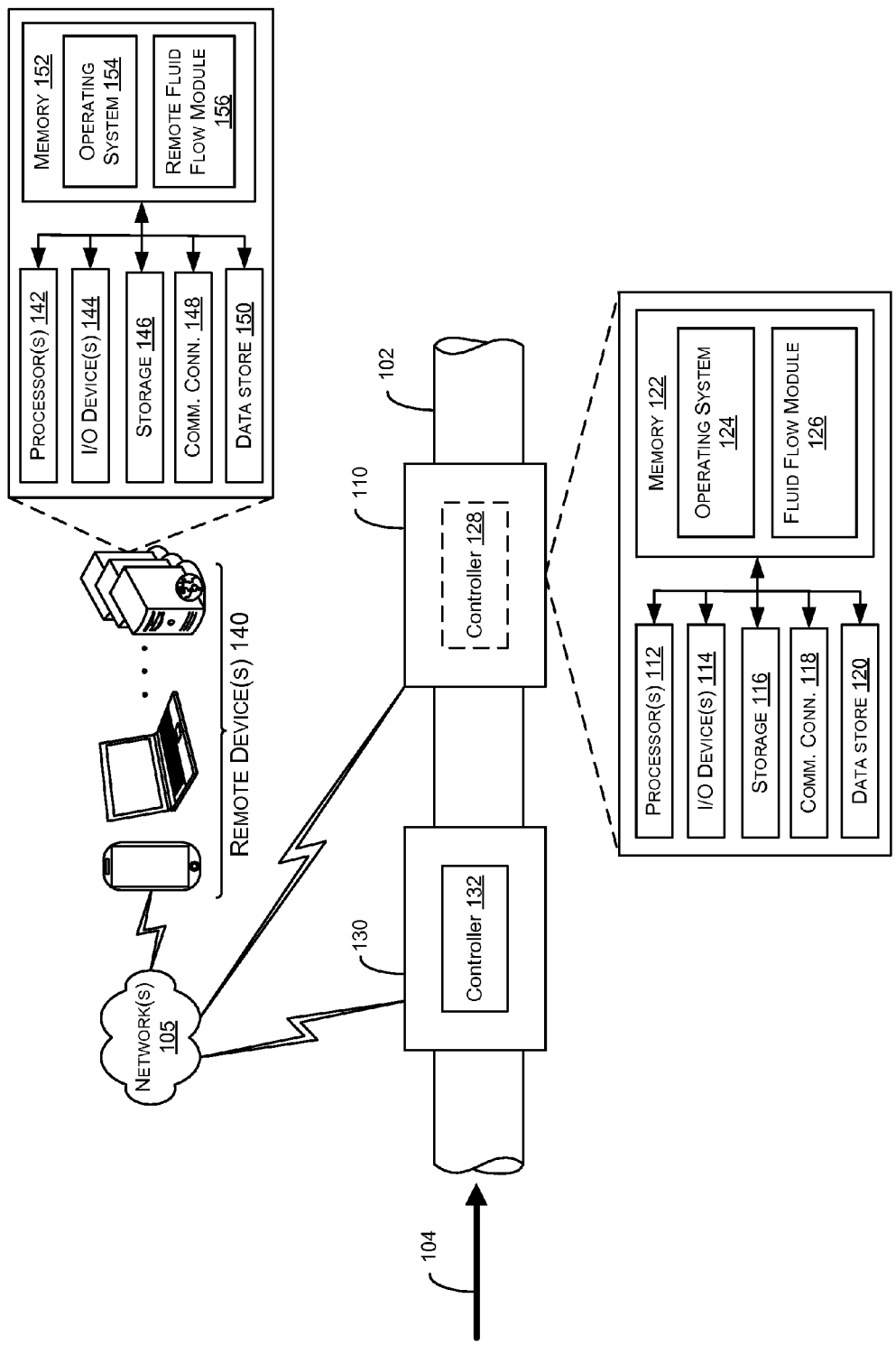
FIG. 1 schematically depicts an example system for determining, among other things, a volumetric flow of a liquid portion of a multiphase fluid flow in accordance with one or more embodiments of the disclosure.

The systems and methods described herein facilitate determining, among other things, a volumetric flow of a liquid portion of a multiphase fluid flow. A multiphase flow is defined as a flow in which more than one phase (i.e., solid, gas, and/or liquid) occurs or a flow having multiples of a single phases (e.g., two liquids). In the oil and gas industry, typical multiphase fluid flows include gas-liquid flows (e.g., gas and oil) and liquid-liquid flows (e.g., water and oil). In many instances, it may only be desirable to know the volumetric flow of one of the phases of a multiphase fluid flow. For example, a pipeline may include an oil and gas mixture flowing therethrough. In this mixture, it may be desirable to know the volumetric flow of the oil portion of the fluid flow. The systems and methods described herein may facilitate the determination of the volumetric flow of the oil portion of the fluid flow, as a non-limiting example, with greater accuracy than current techniques. Although described with reference to the oil and gas industry, the systems and methods described herein may be implemented in any suitable context.

The systems and methods described herein may be based on the assumption that at least some properties associated with a fluid flow are known. For example, an expected density of a fluid flow at an operating condition (such as at a specified temperature or pressure) may be determined from known equations or tables. In this manner, the expected density of the fluid flow may be compared to an actual density of the fluid flow as measured by a mass flow meter. If the difference between the expected density of the fluid flow and the measured density of the fluid flow is greater than an acceptable margin of error, then this may indicate a multiphase fluid flow. For example, if the measured density of the fluid flow is lower than the expected density of the fluid flow, then this may be an indication of a gas-liquid multiphase fluid flow. Conversely, if the measured density of the fluid flow is greater than the expected density of the fluid flow, then this may be an indication of a liquid-liquid multiphase fluid flow, wherein one of the liquids is denser than the other.

When the comparison between the measured density of the fluid flow and the expected density of the fluid flow indicates a gas-liquid multiphase fluid flow, the expected density of the fluid flow may be used to determine a volumetric flow of a liquid portion of the fluid flow. That is, instead of using the measured (i.e., actual) density of the fluid flow, the expected density of the fluid flow may be used to determine the volumetric flow of the liquid portion of the fluid flow. In such instances, using the expected density may provide a more accurate determination of the volumetric flow of the liquid portion than using the measured density. Furthermore, a volume percentage of a gas portion of the fluid flow may be determined using a density ratio between the measured density of the fluid flow and the expected density of the fluid flow.

When the comparison between the measured density of the fluid flow and the expected density of the fluid flow indicates a liquid-liquid multiphase fluid flow, the measured density of the fluid flow may be used to determine a volumetric flow of one of the liquid portions of the fluid flow, such as a less dense liquid portion of the fluid flow. Furthermore, a volume percentage of one of the liquid portions of the fluid flow, such as a denser liquid portion of the fluid flow, may be determined using a density ratio between the measured density of the fluid flow and the expected density of the fluid flow.

In certain embodiments, the fluid flow may comprise more than two liquids. In such instances, if one of the liquids is water, a water cut probe may be incorporated into the systems and methods described herein. With the assistance of the water cut probe, the water portion of the fluid flow may be measured and omitted from the fluid flow when performing the above described operations.

These and other embodiments of the disclosure will be described in more detail with reference to the accompanying drawings in the detailed description of the disclosure that follows. This brief introduction, including section titles and corresponding summaries, is provided for the reader's convenience and is not intended to limit the scope of the claims or the proceeding sections. Furthermore, the techniques described above and below may be implemented in a number of ways and in a number of contexts. Several example implementations and contexts are provided with reference to the following figures, as described below in more detail. However, the following implementations and contexts are but a few of many.

FIG. 1 schematically depicts a system 100 for determining a volumetric flow of a liquid portion of a multiphase fluid flow in accordance with one or more embodiments of the disclosure. The system 100 may include, but is not limited to, a pipe 102 and various computing and/or measurement devices, such as a mass flow meter 110, a water cut probe 130, and one or more remote devices 140. Each of these devices may implement or facilitate the processes described herein. In one embodiment, the mass flow meter 110 may receive a measurement of the amount of water in a fluid 104 flowing through the pipe 102, among other information, and utilize the information to determine a volumetric flow of a liquid portion of a multiphase fluid flow, among other things. In other embodiments, all or at least a portion of the determination may be performed by one or more of the remote devices 140. In such embodiments, the mass flow meter 110 may send at least a portion of the information received from the water cut probe 130 to one or more of the remote devices 140 for processing. In this way, the processes described herein may be distributed among various types and/or numbers of devices that may be configured to communicate over the one or more networks 105 to implement or facilitate the processes described herein. The remote devices 140 may be close to the flow meter 110 and/or the water cut probe 130 or positioned at a remote location from the flow meter 110 and/or the water cut probe 130. Numerous other configurations may exist, at least some of which are described below.

As used herein, the term "device" may refer to any computing component that includes one or more processors that can be configured to execute computer-readable, computer-implemented, or computer-executable instructions. Example devices may include flow meters, personal computers, server computers, server farms, digital assistants, smart phones, personal digital assistants, digital tablets, smart cards, wearable computing devices, Internet appliances, application-specific circuits, microcontrollers, mini-computers, transceivers, kiosks, or other processor-based devices. The execution of suitable computer-implemented instructions by one or more processors associated with various devices may form special purpose computers or other particular machines that may implement or facilitate determining, among other things, a volumetric flow of a liquid portion of a multiphase fluid flow, as described herein.

The one or more networks 105 may include any number of wired or wireless networks that may enable various computing devices in the example healthcare system 100 to communicate with one another. In various embodiments, other networks, intranets, or combinations of different types of networks may be used including, but not limited to, the Internet, intranets, cable networks, cellular networks, landline-based networks, or other communication mediums connecting multiple computing devices to one another. The network 105 may allow for real-time, off-line, and/or batch transactions, as non-limiting examples, to be transmitted between or among the devices shown in the system 100. Due to network connectivity, methodologies as described herein may be practiced in the context of distributed computing environments. Other embodiments may not involve a network and may, for example, provide features on a single device or on devices that are directly connected to one another (for example, the water cut probe 130 may be directly connected to the mass flow meter 110, according to one configuration).

The pipe 102 may have fluid 104 flowing therethrough. In some instances, the pipe 102 may form part of a larger system in an oil and gas application, such as an oil and/or gas well, a refinement facility, a fracking operation, or the like. The fluid flow 104 may be a single phase flow or a multiphase flow. For example, the fluid flow 104 may comprise a liquid flow, a gas flow, or a combination thereof. In some instances, the fluid flow 104 may comprise an oil/gas mixture, an oil/water mixture, or a combination thereof. The fluid flow 104 may be any gas and/or liquid.

The mass flow meter 110 may be coupled to, attached, or otherwise in connection with the pipe 102. The mass flow meter 110 may be configured to measure a mass and/or density of the fluid flow 104. In some instances, the mass flow meter 110 may be a Coriolis mass flow meter.

Each of the mass flow meter 110, the water cut probe 130, and the remote devices 140 may include one or more processors configured to communicate with one or more memory devices and various other components or devices. For example, the mass flow meter 110 may include one or more devices that include one or more processors 112, one or more input/output (I/O) devices 114, storage 116, one or more communication connections 118, and one or more data stores 120. The one or more processors 112 may be implemented as appropriate in hardware, software, firmware, or any combination thereof. The one or more processors 142 associated with the remote devices 140 and a processor (not shown) associated with the water cut probe 130 may be the same or at least similar to the processor 112.

In some embodiments, the mass flow meter 110 may include a controller 128. In one embodiment, the controller 128 may perform all or at least a portion of the functionality associated with the mass flow meter 110. In some instances, the controller 128 may be integrated into the mass flow meter 110. In other instances, the controller 128 may be a distinct component from the mass flow meter 110. The controller 128 may comprise at least one processor, such as processor 112, coupled to at least one memory, such as memory 122. The mass flow meter 110 and/or the controller 128 may be in communication with one or more networks 105.

The memory 122 associated with the mass flow meter 110 may store program instructions that are loadable and executable on the processor 112, as well as data generated during the execution of these programs. Depending on the configuration and type of the mass flow meter 110, the memory 122 may be volatile, such as random access memory (RAM), static random access memory (SRAM), dynamic random access memory (DRAM); or non-volatile, such as read-only memory (ROM), Electrically Erasable Programmable Read-Only Memory (EEPROM), flash memory, etc. The memory 152 associated with the remote devices 140 and a memory (not shown) associated with the water cut probe 130 may be the same or at least similar to the memory 122 associated with the mass flow meter 110, in one embodiment.

The storage 116 associated with the mass flow meter 110 may include removable and/or non-removable storage including, but not limited to, magnetic storage, optical disks, and/or tape storage. The disk drives and their associated computer-readable media may provide non-volatile storage of computer-readable instructions, data structures, program modules, and other data for the computing system. The storage 146 associated with the remote devices 140 and a storage (not shown) associated with the water cut probe 130 may be the same or at least similar to the storage 116 associated with the mass flow meter 110, in one embodiment.

The memories 122 and 152, and the storages 116 and 146, both removable and non-removable as well as the memory and storage (not shown) for the water cut probe 130, are all examples of computer-readable storage media. For example, computer-readable storage media may include volatile and non-volatile, removable and non-removable media implemented in any method or technology for storage of information such as computer-readable instructions, data structures, program modules, or other data.

The I/O devices 114 associated with the mass flow meter 110 may enable a user to interact with the mass flow meter 110 to perform various functions. The I/O devices 114 may include, but are not limited to, a keyboard, keypad, selector buttons/knobs/wheels, a mouse, a pen, a voice input device, a touch input device, a gesture detection or capture device, a display, a camera or an imaging device, speakers, and/or a printer. The I/O devices 114 associated with the remote devices 140 may be the same or at least similar to the I/O devices 114, in one embodiment.

The one or more communication connections 118 associated with the mass flow meter 110 may allow the mass flow meter 110 to communicate with other devices, such as the remote devices 140, via the one or more networks 105. The communication connections 118 may include one or more antennas and one or more radios, which may include hardware and software for sending and/or receiving wireless signals over the various types of networks 105 described above. The communication connections 148 associated with the remote devices 140 may be the same or similar to the communication connections 118, in one embodiment. Moreover, the water cut probe 130 may include communication connections (not shown) that may be the same or similar to the communication connections 118 and/or communication connections 148.

The one or more data stores 120 may store lists, arrays, databases, flat files, etc. In some implementations, the data store 120 may be stored in a memory external to the mass flow meter 110 but may be accessible via one or more networks 105, such as with a cloud storage service. The data store 120 may store information that may facilitate the processes described herein, such as the determination of a volumetric flow of a liquid portion of a multiphase fluid flow. Non-limiting examples of such information are described herein. The data stores 150 of the remote devices 140 may be the same or at least similar to the data stores 120, in one embodiment.

Turning to the contents of the memory 122 in more detail, the memory 122 may include an operating system 124 and one or more application programs or services for implementing the features disclosed herein, such as a fluid flow module 126. The fluid flow module 126 may be configured to receive, store, determine, identify, and/or provide information associated with the mass flow meter 110 and the water cut probe 130. For example, the fluid flow module 126 may be configured to determine an expected density of the fluid flow 104 at an operating condition, such as temperature or pressure. In some instances, the expected density of the fluid flow 104 may be determined using known tables or equations based on one or more known properties (or expected properties) of the fluid flow 104. The expected density of the fluid flow 104 may be stored in the data store 120, such as a database or other storage mechanism, whether local or remotely accessible via the one or more networks 105.

The fluid flow module 126 may also be configured to compare the expected density of the fluid flow 104 to a measured density of the fluid flow 104. In some instances, the measured density of the fluid flow 104 may be determined by the mass flow meter 110. Moreover, the fluid flow module 126 may be configured to determine, based at least in part on the expected density compared to the measured density of the fluid flow 104, a phase status of the fluid flow 104. That is, the fluid flow module 126 may be configured to determine whether the fluid flow 104 is a single phase flow or a multiphase flow. If the difference between the expected density of the fluid flow 104 and the measured density of the fluid flow 104 is greater than an acceptable margin of error (for example, greater than or equal to 3% or any percentage whether predetermined, known, calculated, etc.), then this may indicate a multiphase fluid flow. The acceptable margin may be any percentage, number, or determined otherwise. For example, if the measured density of the fluid flow 104 is less than the expected density of the fluid flow 104, then this may be an indication of a gas-liquid multiphase fluid flow. Conversely, if the measured density of the fluid flow 104 is greater than the expected density of the fluid flow 104, then this may be an indication of a liquid-liquid multiphase fluid flow, wherein one of the liquids is denser than the other.

The fluid flow module 126 may be further configured to determine a volumetric flow of a liquid portion of the fluid flow 104 using the expected density of the fluid flow 104 if the measured density of the fluid flow 104 is less than the expected density of the fluid flow 104. That is, when the comparison between the measured density of the fluid flow 104 and the expected density of the fluid flow 104 indicates a liquid-gas multiphase fluid flow, the expected density of the fluid flow 104 may be used to determine the volumetric flow of the liquid portion of the fluid flow 104. In such instances, using the expected density may provide a more accurate determination of the volumetric flow of the liquid portion than using the measured density.

The fluid flow module 126 may be further configured to determine, based at least in part on the measured density of the fluid flow 104 and the expected density of the fluid flow 104, a volume percentage of a gas portion of the fluid flow 104. That is, the volume percentage of the gas portion of the fluid flow 104 may be determined using a density ratio between the measured density of the fluid flow 104 and the expected density of the fluid flow 104.

If the measured density of the fluid flow 104 is greater than the expected density, then the fluid flow module 126 may be configured to determine a volumetric flow of one of the liquid portions of the fluid flow 104 using the measured density of the fluid flow 104. That is, when the comparison between the measured density of the fluid flow 104 and the expected density of the fluid flow 104 indicates a liquid-liquid multiphase fluid flow, the measured density of the fluid flow 104 may be used to determine a volumetric flow of one of the liquid portions of the fluid flow 104, such as the less dense liquid portion of the fluid flow 104.

The fluid flow module 126 may be further configured to determine, based at least in part on the measured density of the fluid flow 104 and the expected density of the fluid flow 104, a volume percentage of one of the liquid portions of the fluid flow 104. That is, the volume percentage of, for example, the denser liquid portion of the fluid flow 104 may be determined using a density ratio between the measured density of the fluid flow 104 and the expected density of the fluid flow 104.

In certain embodiments, the fluid flow 104 may comprise more than two liquids. In such instances, if one of the liquids is water, the fluid flow module 126 may be configured to omit the water portion of the fluid flow 104 when performing the above described operations. For example, the fluid flow module 126 may be configured to receive a water measurement from the water cut probe 130. Based on the water measurement, the fluid flow module 126 may omit the calculated water portion from the fluid flow/density calculations when performing the above described operations.

The above processes described in association with the mass flow meter 110 are for purposes of illustration and are not meant to be limiting. Various other processes may be performed by the fluid flow module 126 and/or one or more other modules.

In some embodiments, all or at least a portion of the functionality performed by the mass flow meter 110 may be performed by one or more of the remote devices 140. As shown in FIG. 1, the memory 152 of the remote device 140 may include an operating system 154 and a remote fluid flow module 156 for implementing such functionality. In one embodiment, the remote fluid flow module 156 may receive various information, such as but not limited to, a measured density and a calculated density (for example, based on known or expected properties). Such information may be received from the mass flow meter 110, a data store accessible via the one or more networks 105, other devices, etc. Upon receiving the information, the remote devices 140 may perform the comparisons and determinations described above in association with the mass flow meter 110. At least a portion of the determinations or results may be stored and/or distributed to the mass flow meter 110 and/or various other devices.

As mentioned, the water cut probe 130 may be configured to measure an amount of water in the fluid flow 104. In some instances, the water cut probe 130 may be integrated into the mass flow meter 110. In other instances, the water cut probe 130 may be a separate and distinct component from the mass flow meter 110. The water cut probe 130 may include a controller 132. In some instances, the controller 132 may be integrated into the water cut probe 130. In other instances, the controller 132 may be a separate and distinct component from the water cut probe 130. The controller 132 may include at least one processor coupled to at least one memory. The water cut probe 130 and/or the controller 132 may be in communication with the one or more networks 105. In some embodiments, one or more processors, memories, etc., separate from the controller 132 may exist in the water cut probe 130 for measuring an amount of water in the fluid flow 104, among other functions.

Although the above operations are described as being implemented by the mass flow meter 110, they may equally be implemented at one or more of the remote devices 140, the water cut probe 130, by a third-party computing device in communication with the one or more networks 105, or any combination thereof. That is, any device or combination of devices may be used to implement the above operations. The example architecture is but a few of many. The specific architectures, features, and acts are disclosed as example illustrative forms of implementing the embodiments.

In further illustrative embodiments, mass flow meters (such as Coriolis mass flow meters) are capable of measuring mass flow and density of fluid flows with relatively high accuracy. This is typically true even when gas is entrained in the fluid flow. Mass flow meters, however, may not be capable of directly measuring the volumetric flow of the fluid flow. Instead, the volumetric flow of the fluid flow may be calculated as follows:

$$\dot{v} = \frac{\dot{m}_{measured}}{\rho_{measured}} \quad (1)$$

For pure liquid fluid flows, the accuracy of the volumetric flow calculation may depend on the combined uncertainty of the mass flow and the density measurement. If there is entrained gas (i.e., Gas Void Fraction (GVF)) in the fluid flow, the above calculation may be performed to determine volumetric flow. For low GVF, the mass flow may remain almost unchanged because it is determined mainly by the mass flow of the liquid portion of the fluid flow. On the other hand, the density of the fluid flow may drop significantly due to the entrained gas therein. As a result, the indicated volumetric flow and the totalized volume of the multiphase fluid flow may be higher as compared to a pure liquid single phase fluid flow.

In a typical oil and gas application, it may be desirable to know the volumetric flow of only a liquid portion of a multiphase fluid flow. That is, the entrained gas portion of the multiphase fluid flow may be an unwanted condition. In many instances, the entrained gas may evaporate from the fluid flow. For example, the entrained gas may evaporate in a storage tank or the like. In this manner, if the volume of the liquid in the storage tank is compared to the volume of the fluid flow as indicated by the mass flow meter, a deviation may occur.

An indication of GVF may be a drop in the measured operating density of the fluid flow. This may be detected when the expected density of the liquid is known. For instance, the expected density of water may be calculated according to the International Association for the Properties of Water and Steam (IAPWS), and the expected density of oil can be calculated according to the American Petroleum Institute (API). For liquids, in general, the expected density may be calculated as follows:

$$\text{expected density: } \rho = \frac{\rho_{ref}}{1 + a*(T - T_{ref}) + b*(T - T_{ref})^2} \quad (2)$$

A reference density $\rho_{ref}$ and a reference temperature ($T_{ref}$) are usually known. The linear thermal expansion coefficient a may be found in literature for most liquids, and a linear approach may be sufficient for a limited density and temperature (T) range. Based on the expected density of the fluid flow, GVF may be detected by comparing the measured operating density of the fluid flow with the expected liquid density of the fluid flow:

$$\text{GVF present if: } \rho_{measured} < \rho_{expected} \quad (3)$$

As discussed above, the entrained gas portion of the fluid flow may typically be neglected. That is, only the volume of the liquid portion of the fluid flow may be of importance. In such instances, the volume of the liquid portion of the fluid flow may be calculated by replacing the measured operating density with the expected liquid density:

$$\text{if GVF present, then: } \rho_{measured} = \rho_{expected} \quad (4)$$

By replacing the measured operating density with the expected liquid density, the volumetric flow of the liquid portion of the fluid flow may be calculated by using the expected density of the liquid portion of the fluid flow:

$$\text{if } GVF \text{ present: } \dot{v} = \frac{\dot{m}_{measured}}{\rho_{expectedd}} \quad (5)$$

In addition to the detection of entrained gas in the fluid flow, it is also possible to determine the amount of entrained gas in the fluid flow. The GVF as a volume percentage may be calculated by the ratio of the measured and expected densities:

$$\text{if } GVF \text{ present: } GVF = \left(1 - \frac{\rho_{measured}}{\rho_{expected}}\right) * 100\% \quad (6)$$

In addition to the detection of entrained gas in the fluid flow, the systems and methods described herein may be implemented to detect the presence of another denser liquid in the multiphase flow. For example:

$$\text{denser liquid present if: } \rho_{measured} > \rho_{expected} \quad (7)$$

An example may be water in oil. In such instances, the amount of the denser liquid may be determined as a volume percentage:

$$\text{if denser liquid present: vol}\% = \left(\frac{\rho_{measured}}{\rho_{expected}} - 1\right) * 100\% \quad (8)$$

In the case of two liquids, to determine the volumetric flow of the desired component of the fluid flow, a net flow calculation may be performed:

$$\text{if denser liquid present: } \dot{v} = \frac{\dot{m}_{measured}}{\rho_{measured}} * (100\% - \text{vol}\%) \quad (9)$$

The aforementioned operations are directed to fluid flows comprising GVF or two different liquids. However, in certain embodiments, the fluid flow may comprise more than two liquids. In such instances, if one of the components is water, a water cut probe (for example, the water cut probe 130 in FIG. 1) may be incorporated to omit the water portion. Once the water is removed from the fluid flow, the above described operations may be implemented. Water cut probes may measure the amount of water as a volume percentage, while Coriolis mass flow meters may measure the mass flow. To subtract the amount of water from the fluid flow, the density of the remaining components without water may be determined:

$$\text{density of the mixture without water: } \rho_{mix} = \frac{\rho_{measured}}{\frac{\text{vol }\%}{100\%} + 1} \quad (10)$$

The measured operating density may then be replaced by the calculated density of the fluid flow without water:

$$\text{replacement of measured density: } \rho_{measured} = \rho_{mix} \quad (11)$$

With this new value for the measured density, the GVF check according to operation (3) or the denser liquid check according to operation (7) may be performed. For instance, if the application is a mixture of water, oil, and gas, the Coriolis mass flow and density meter may behave as if it measured only oil and gas after this operation. Thus, the three-phase flow may be reduced to a two-phase flow.

The above determinations and calculations are for purposes of illustration and are not meant to be limiting. Other determinations, calculations, considerations, etc., may exist in other examples.

Figure 2:
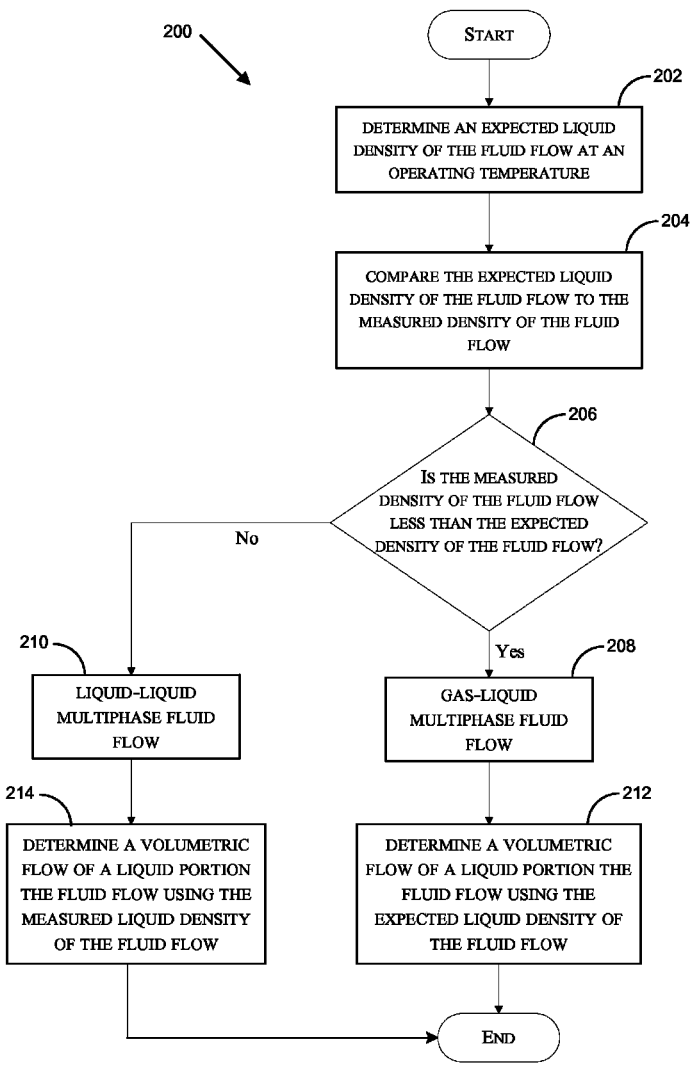
FIG. 2 is a flow diagram depicting an illustrative method for determining, among other things, a volumetric flow of a liquid portion of a multiphase fluid flow in accordance with one or more embodiments of the disclosure.

FIG. 2 is a flow diagram depicting an illustrative method 200 for determining a volumetric flow of a liquid portion of a multiphase fluid flow in accordance with one or more embodiments of the disclosure. In one embodiment, all or a portion of the illustrative method 200 may be performed by the mass flow meter 110 in FIG. 1. Further, all or a portion of the illustrative method 200 may be performed by any combination of the mass flow meter 110, the water cut probe 130, and a remote device 140.

The illustrative method 200 may begin at block 202, where an expected liquid density of a fluid flow (for example, the fluid flow 104) at an operating temperature or pressure may be determined. In some instances, the expected density of the fluid flow may be determined using known tables or equations based on one or more known properties (or expected properties) of the fluid flow. For example, the mass flow meter may retrieve the expected liquid density of a fluid flow from data store 120. At block 204, the mass flow meter 210 may measure the actual density of the fluid flow 104, and the mass flow meter 110 may compare the expected liquid density of the fluid flow to the measured density of the fluid flow. At block 206, a phase status of the fluid flow may be determined based at least in part on a comparison of the expected density to the measured density of the fluid flow. In one embodiment, the phase status is determined by the mass flow meter 110. Alternatively, the mass flow meter 110 may transmit the measured density to the remote device 140 via the network 105 and the remote device 140 may determine the phase status. For example, at block 208, if the measured density of the fluid flow 104 is lower than the expected density of the fluid flow 104, then this may be an indication of a gas-liquid multiphase fluid flow. Conversely, at block 210, if the measured density of the fluid flow 104 is greater than the expected density of the fluid flow 104, then this may be an indication of a liquid-liquid multiphase fluid flow, wherein one of the liquids may be denser than the other.

If the measured density of the fluid flow is less than the expected density of the fluid flow, the process can proceed to block 212, where a volumetric flow of a liquid portion of the fluid flow may be determined using the expected density of the fluid flow. That is, when the comparison between the measured density of the fluid flow and the expected density of the fluid flow indicates a liquid-gas multiphase fluid flow, the expected density of the fluid flow may be used to determine the volumetric flow of the liquid portion of the fluid flow 104. In one embodiment, the volumetric flow determination may be made by the mass flow meter 110. Alternatively, the remote device 140 may determine the volumetric flow of the liquid portion of the fluid flow 104. In such instances, using the expected density may provide a more accurate determination of the volumetric flow of the liquid portion than using the measured density.

If the measured density of the fluid flow is greater than the expected density of the fluid flow, the process can proceed to block 214, where a volumetric flow of one of the liquid portions of the fluid flow may be determined using the measured density of the fluid flow. That is, when the comparison between the measured density of the fluid flow and the expected density of the fluid flow indicates a liquid-liquid multiphase fluid flow, the measured density of the fluid flow may be used to determine a volumetric flow of one of the liquid portions of the fluid flow, such as the less dense liquid portion of the fluid flow, in one embodiment. In one embodiment, the volumetric flow determination may be made by the mass flow meter 110. Alternatively, the remote device 140 may determine the volumetric flow of one of the liquid portions of the fluid flow 104.

Figure 3:
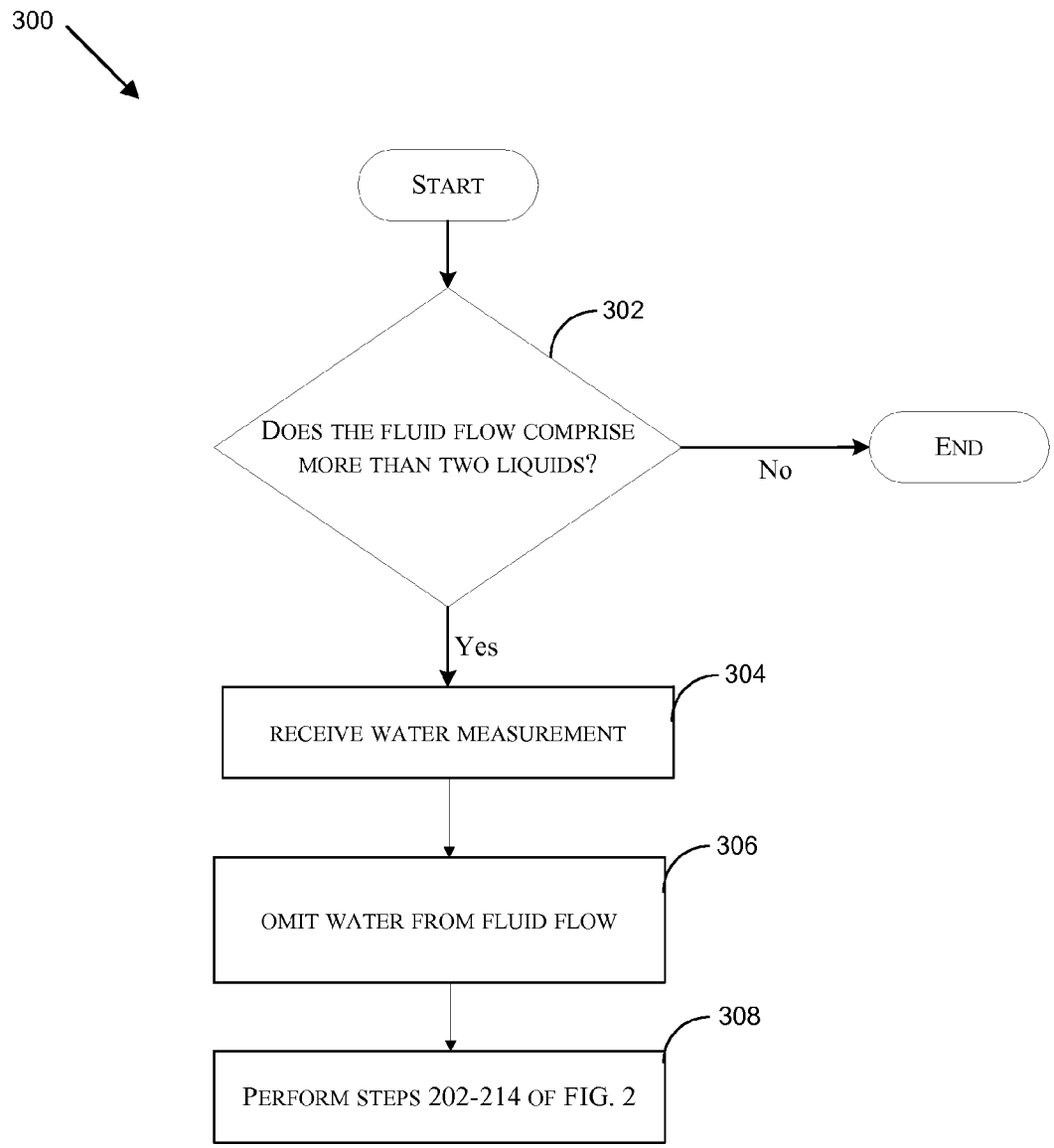
FIG. 3 is a flow diagram depicting an illustrative method for determining, among other things, a volumetric flow of a liquid portion of a multiphase fluid flow in which one of the phases is water, in accordance with one or more embodiments of the disclosure.

FIG. 3 is a flow diagram depicting an illustrative method 300 for determining a volumetric flow of a liquid portion of a multiphase fluid flow, wherein one of the phases is water. In one embodiment, the illustrative method 300 may be performed by the mass flow meter 110 in FIG. 1.

The illustrative method 300 may begin at block 302, where it may be determined if a fluid flow (for example, the fluid flow 104) includes more than two liquids. For example, in certain embodiments, a water cut probe (for example, the water cut probe 130) may be configured to measure an amount of water in the fluid flow. In such instances, if one of the liquids is determined to be water, the water cut probe 130 may determine the portion of the volumetric fluid flow that is water and may provide this determination to one or both of the mass flow meter 110 and the remote device 140 so that the water portion of the fluid flow may be omitted when performing the operations described in FIG. 2. For example, at block 304, a water measurement may be received from the water cut probe 130. For example, the water measurement may be the volume of water that makes up or is included in the fluid flow 104. Based on the water measurement, at block 306, the water portion of the fluid flow may be omitted from the fluid flow. After the water has been omitted from the fluid flow, the steps of the method 200 in FIG. 2 may be performed at block 308.

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

Certain aspects of the disclosure are described above with reference to block and flow diagrams of systems, methods, apparatuses, and/or computer program products according to various implementations. It will be understood that one or more blocks of the block diagrams and flow diagrams, and combinations of blocks in the block diagrams and the flow diagrams, respectively, can be implemented by computer-executable program instructions. Likewise, some blocks of the block diagrams and flow diagrams may not necessarily need to be performed in the order presented, or may not necessarily need to be performed at all, according to some implementations.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments.

Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A Coriolis mass flow meter comprising a controller configured to:
    determine an expected liquid density of an oil fluid flow at an operating temperature as determined by $$\rho = \frac{\rho_{ref}}{1 + a*(T - T_{ref}) + b*(T - T_{ref})^2};$$

measure the density of the oil fluid flow;
    compare the expected liquid density of the oil fluid flow to the measured density of the oil fluid flow;
    determine, based at least in part on the expected liquid density compared to the measured density of the oil fluid flow, a phase status of the oil fluid flow, wherein when the measured density of the oil fluid flow is less than the expected liquid density of the oil fluid flow, the phase status of the oil fluid flow comprises an oil/gas fluid flow;
    determine, when the measured density of the oil fluid flow is less than the expected liquid density of the oil fluid flow, a volumetric flow of an oil portion of the oil/gas fluid flow using the expected liquid density of the oil fluid flow; and
    determine, when the measured density of the oil fluid flow is less than the expected liquid density of the oil fluid flow and based on a density ratio as determined by $$GVF = \left(1 - \frac{\rho_{measured}}{\rho_{expected}}\right)*100\%$$

in the specification, a volumetric flow of a gas portion of the oil/gas fluid flow.

2. A system, comprising:
    a pipe having an oil fluid flow therethrough;
    a Coriolis mass flow meter coupled to the pipe, wherein the Coriolis mass flow meter is configured to measure a density of the oil fluid flow in the pipe, the Coriolis mass flow meter comprising:
        at least one memory that stores computer-executable instructions; and
        at least one processor configured to access the at least one memory, wherein the at least one processor is configured to execute the computer-executable instructions to:
            determine an expected liquid density of the oil fluid flow at an operating temperature as determined by $$\rho = \frac{\rho_{ref}}{1 + a*(T - T_{ref}) + b*(T - T_{ref})^2};$$

compare the expected liquid density of the oil fluid flow to the measured density of the oil fluid flow; and determine, based at least in part on the expected liquid density compared to the measured density of the oil fluid flow, a phase status of the oil fluid flow, wherein when the measured density of the oil fluid flow is less than the expected liquid density of the oil fluid flow, the phase status of the oil fluid flow comprises an oil/gas fluid flow;

determine, when the measured density of the oil fluid flow is less than the expected liquid density of the oil fluid flow, a volumetric flow of an oil portion of the oil/gas fluid flow using the expected liquid density of the oil fluid flow; and determine, when the measured density of the oil fluid flow is less than the expected liquid density of the oil fluid flow and based on a density ratio as determined by $$GVF = \left(1 - \frac{\rho_{measured}}{\rho_{expected}}\right) * 100\%,$$

a volumetric flow of a gas portion of the oil/gas fluid flow.

3. The system of claim 2, wherein the at least one processor is further configured to execute the computer-executable instructions to omit a calculated amount for water that makes up a portion of the fluid flow.

4. The system of claim 3, further comprising a water cut probe coupled to the pipe.

\* \* \* \* \*